United States Patent [19]

Zentner et al.

[11] Patent Number: 4,780,319

[45] Date of Patent: Oct. 25, 1988

[54] ORGANIC ACIDS AS CATALYSTS FOR THE EROSION OF POLYMERS

[75] Inventors: Gaylen M. Zentner, Lawrence, Kans.; Kenneth J. Himmelstein, Irvine, Calif.; Stefano A. Pogany, Lawrence; Cheryl Ringeisen, Olathe, both of Kans.

[73] Assignee: Merck & Co., Inc., Rahway, N.J.

[21] Appl. No.: 33,565

[22] Filed: Apr. 3, 1987

Related U.S. Application Data

[63] Continuation-in-part of Ser. No. 752,436, Jul. 8, 1985, abandoned.

[51] Int. Cl.$^4$ .................. A61K 31/19; A61K 31/20
[52] U.S. Cl. .................. 424/476; 424/405; 424/409; 424/422; 424/482; 424/486; 424/78; 523/124; 523/125; 523/126; 523/127
[58] Field of Search .................. 523/124–128; 424/78, 405, 409, 422, 476, 482, 486

[56] References Cited

U.S. PATENT DOCUMENTS

| | | | |
|---|---|---|---|
| 3,383,283 | 5/1968 | Brindamour | 424/476 |
| 3,825,626 | 7/1974 | McGaugh | 523/124 |
| 4,056,665 | 11/1977 | Taylor et al. | 523/127 |
| 4,093,709 | 6/1978 | Choi et al. | 424/78 |
| 4,304,767 | 12/1981 | Heller et al. | 424/78 |
| 4,374,938 | 2/1983 | Verhelst et al. | 523/124 |
| 4,489,056 | 12/1984 | Himmelstein et al. | 424/78 |

FOREIGN PATENT DOCUMENTS

| | | | |
|---|---|---|---|
| 285091 | 6/1929 | United Kingdom | 424/476 |
| 1401418 | 7/1975 | United Kingdom | 523/126 |

Primary Examiner—Ronald W. Griffin
Attorney, Agent, or Firm—Manfred Polk; Michael C. Sudol

[57] ABSTRACT

The invention relates to the use of carboxylic acids incorporated as a catalyst in poly(orthoester)s and other acid labile polymers such that upon exposure to aqueous environments the acid catalyzes the erosion of the polymer matrix. The rate of release of a drug substance incorporated into or surrounded by the poly(orthoester) or other acid labile polymer can be controlled in that the drug is released as the polymer is eroded in response to the catalytic action of the acid incorporated therein.

11 Claims, 5 Drawing Sheets

Figure 1:
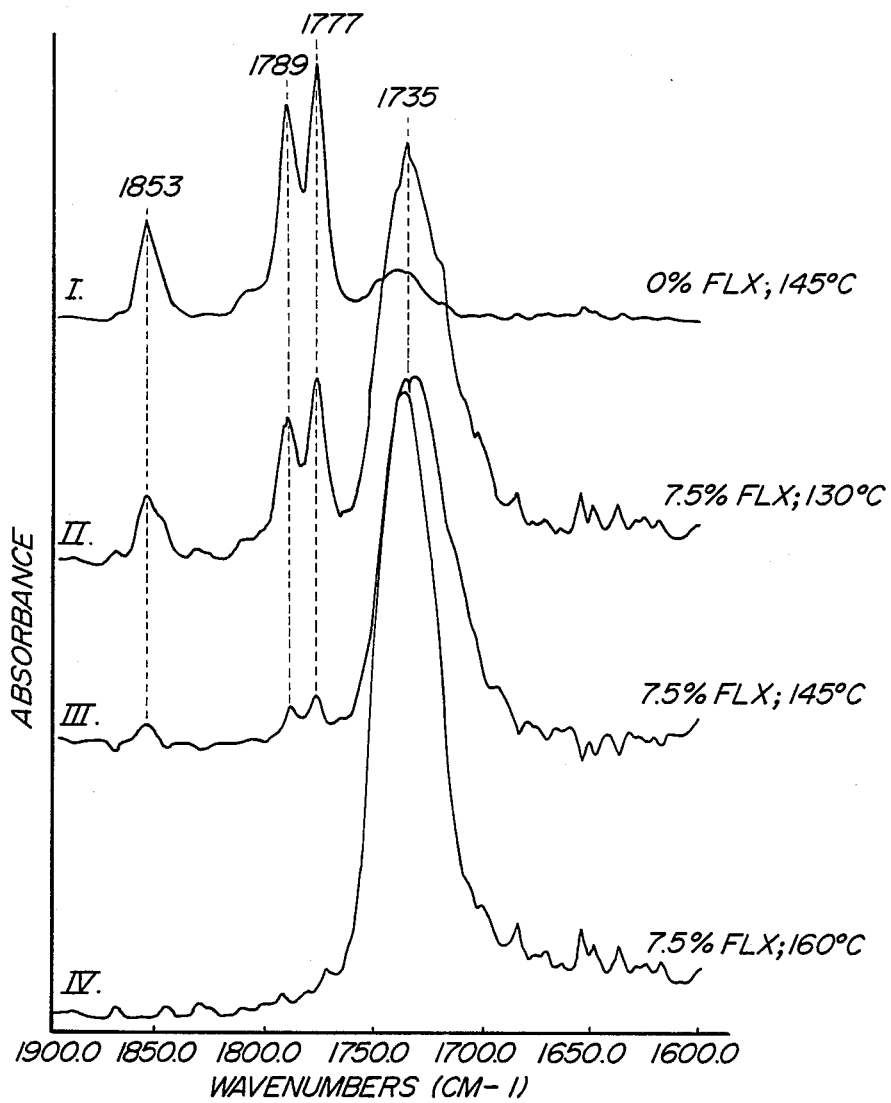

FIG-1 INFRARED SPECTRA OF PHTHALIC ANHYDRIDE IN POLY(ORTHO ESTER): CONVERSION OF ANHYDRIDE TO ESTER DERIVATIVES VIA REACTION WITH DRUG AND POLYMER CONSTITUENTS.

FIG-2 PHTHALIC ANHYDRIDE/POLY(ORTHO ESTER PHTHALIC ANHYDRIDE CONTENT

FIG-3 PHTHALIC ANHYDRIDE/POLY(ORTHO ESTER HEXANEDIOL MONOPHTHALATE

FIG-4 PHTHALIC ANHYDRIDE/POLY(ORTHO ESTER CYCLOHEXANDIMETHANOL MONOPHTHALATE

ORGANIC ACIDS AS CATALYSTS FOR THE EROSION OF POLYMERS

BACKGROUND OF THE INVENTION

This is a continuation-in-part of U.S. application Ser. No. 752,436, filed July 8, 1985, now abandoned.

There has been a long need in the field of drug delivery devices to have a drug released in the human body at the place where it is most therapeutically effective and to have said drug released in the body in a controlled manner over a long period of time.

There is art showing that poly(orthoester)s can be used as a matrix for drug release; however, there is no description in any of this art of the use of organic acids as catalysts to promote the polymer erosion in a controlled fashion.

U.S. Pat. No. 4,489,056 discloses the use of acid anhydrides as catalysts for the erosion of poly(orthoester)s. The patent discloses that the acid anhydride in an aqueous environment generates the corresponding acid. Acid anhydrides may in certain instances have the disadvantage, however, that they are reactive electrophiles that can acylate drugs containing a nucelophilic group, such as a hydroxyl, amino, carboxyl or sulfhydryl group. For example, when phthalic anhydride is used to catalyze the erosion of poly(orthoester)s, significant quantities of phthalic esters of hexane diol, one of the diols which are monomers of the poly(orthoester), are observed. Similarly when timolol, a drug with a hydroxyl functionality, is incorporated into a poly(orthoester) with phthalic anhydride, a significant amount of timolol phthalate ester is observed. Similar reaction products are not observed when free acids, which are not acylating agents, are used as the acid catalysts.

The release of norethindrone from poly(orthester)s slabs has been described in the prior art. However, in this system a water-soluble salt such as sodium chloride and the like was incorporated into the polymer and the proposed mechanism for drug release in this case was osmotic imbibing of water, causing the matrix to swell and burst. The drug release was not controlled by polymer erosion but by a swelling process.

DESCRIPTION OF THE INVENTION

The present invention is directed to a controlled release device for the delivery of drugs or other biological beneficial substances which comprises:
 (a) acid labile polymers, in particular a poly(orthoester) polymer, and
 (b) an erosion catalyzing amount up to a maximum of about 25 percent, by weight, based on (a), of at least one organic acid selected from the group consisting of carboxylic acids and mixtures thereof, incorporated within the matrix of said poly(orthoester).

The rate of release of therapeutically effective drug substance(s) or other beneficial substances (hereafter collectively referred to as biologically active agents) incorporated into or surrounded by such polymer/acid catalyst mixtures is determined by the erosion pattern of the polymer resulting in controlled drug release.

It has been noted that poly(orthoester)s polymer linkages herein described are unstable at acidic pH but relatively stable at neutral or basic pH. Thus, a carboxylic acid which is incorporated into the polymer matrix would catalyze the matrix erosion. If, in addition, a pharmaceutical or therapeutic agent(s) or drug(s) or biologically active agent(s) is incorporated in the matrix of the polymer, it can be seen that the biologically active agent(s) can be released at a predictable rate from the polymer matrix as the polymer matrix is eroded by action of the acid. Also the polymer/acid matrix could surround the drug or beneficial substance whereby the drug or substance will be released when the polymer/acid matrix coating is eroded. The expected mechanism for breakdown and erosion of the polymer can be shown by the following equations where R is as defined further along.

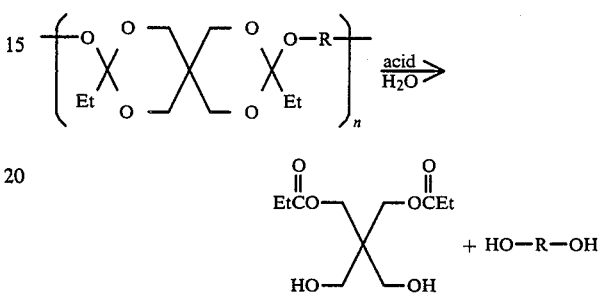

The rate of polymer matrix erosion and subsequently the rate of release of any drug(s) or biologically active agent(s) incorporated into or surrounded by the matrix can be controlled by choosing the proper acid or combination of acids. In selecting appropriate acids as catalysts the pKa, melting point, concentration, and hydrophobic character of the acids must be considered concomitantly for each poly(orthoester) system. For example, phthalic acid (melting point 230°) and the various phthalamic acid derivatives (melting points 100° C.) discussed in the Examples section of the present invention have very similar first pKa's yet catalyze the erosion of the poly(orthoester) DETOSU-1,6-hexanediol:-trans-cyclohexanedimethanol (65:35) differently; increased hydrophobicity and lower melting points of the acids correlated with improved catalytic behavior. In the same poly(orthoester) polymer, p-toluene sulfonic acid (pKa 1; m.p.=100° C.) was an ineffective acid catalyst whereas phthalamic acid derivatives which had significantly higher pKa's were effective catalysts. Again, the increased hydrophobicity of the phthalamic acid derivatives relative to the p-toluene sulfonic acid played an important role. Thus it is clear that acid catalyst selection is sensitive to multiple features of the acid that can be manipulated to give the balance of pKa, melting point, and hydrophobicity to achieve the desired erosion rate of the polymer. Also, the concentration of the acid incorporated into the polymer matrix will control the rate of erosion of the polymer matrix and subsequently the rate of release of the drug substance incorporated therein. We have observed a linear relationship between the concentration of the acid incorporated and the rate of release of the drug substance and rate of erosion of the polymer when the drug or beneficial substance is incorporated in the polymer/acid matrix.

When the drug or beneficial substance is surrounded or coated by the polymer/acid matrix, the drug or beneficial substance can be discharged when the matrix erodes in a predictable time frame.

In a more detailed description of the invention, the following types of polymers and acids are representative of those that can be used. Also there are described representative types of pharmaceuticals, therapeutic agents, biologically acitve agents or drugs or beneficial substances which can be incorporated into or surrounded by the matrix of said polymer to be released by reaction of the acid which catalyzes the matrix erosion.

Although any poly(orthoester) may be used, those described in U.S. Pat. Nos. 4,304,767 and 4,903,709, which are hereby incorporated by reference, are preferred.

Examples of poly(orthoester)s and other acid labile polymers disclosed in these two patents include:

1. Polymers of di(or higher functionality) keteneacetals and polyols which have a repeating mer unit of

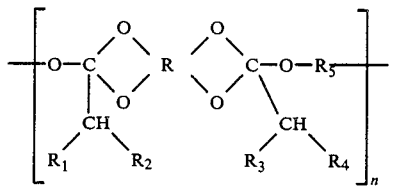

wherein n is an integer substantially greater than 10; preferably 30 to 100. $R_1$ and $R_2$ are hydrogen or the same or different essentially hydrocarbon groups and may be separate groups or may form parts of a cyclic group. Preferably $R_1$ is hydrogen and $R_2$ is methyl, ethyl, propyl, or the reverse. R is a quadrivalent organic grouping; preferably $C_5$ to $C_{30}$. $R_3$ and $R_4$ are hydrogen or the same or different essentially hydrocarbon groups and may be separate groups or may form parts of a cyclic group. Preferably $R_3$ is hydrogen and $R_4$ is methyl, ethyl, propyl, or the reverse. $R_5$ is an essentially hydrocarbon group which is the residue of a polyol $R_5(OH)_a$ wherein a is an integer equal to two or more, preferably 2 to 4, such polyol being a single molecular species or a mixture of molecular species; and wherein such linear chain may be crosslinked with other similar chains, and wherein $R_5$ may be a single quadrivalent radical attached to all the interim acetal forming oxygen atoms, may be a spiro structure, may be an open chain aliphatic group, or may contain a carbocyclic group. For example, $R_5$ may be a linear six carbon chain or 1,4-dimethyl cyclohexane or the like. Additionally, $R_5$ may contain units that are alkylene or contain a carbocyclic group. Also included are polymers having the repeat units

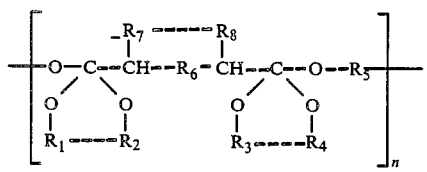

wherein n is an integer substantially greater than 10, preferably 30 to 100, wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group. Preferably $R_1$, $R_2$, $R_3$, and $R_4$ are methyl, ethyl, propyl or combinations thereof and the like. $R_5$ is an essentially hydrocarbon group which is the residue of a polyol $R_5(OH)_a$ wherein a is an integer equal to two or more, preferably 2 to 4, and $R_5$ is as defined previously, such polyol being a single molecular species or a mixture of molecular species; $R_6$ is a valence bond or an essentially hydrocarbon group; $R_7$ and $R_8$ are hydrogen or essentially hydrocarbon groups which may be separate groups or may form parts of a cyclic group; and wherein such linear chains may be crosslinked to similar chains are also part of our invention. The group

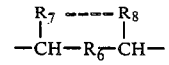

may be selected from the classic alkylene end groups containing a carbocyclic ring.

2. Poly(orthoester) or polyorthocarbonate polymers of the formula:

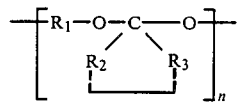

wherein $R_1$ is a multivalent hydrocarbon radical preferably $C_1$ to $C_{30}$. $R_2$ and $R_3$ are hydrocarbon radicals, for example methyl, ethyl, propyl and the like, with at least one of $R_2$ and $R_3$ bonded to the dioxycarbon through an oxygen linkage and n is a repeating mer unit preferably between 30 and 200.

3. Other broad classes of polymers to which this invention is applicable are those polymers with backbone functionalities which are sensitive to acid. Examples of these include polyacetals and polyketals of the formula:

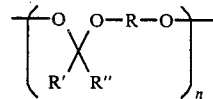

wherein R', R" is H, alkyl or aryl, R is alkylene or arylene and n is a repeating mer unit with an integer value of 30 to 200.

4. Polyesters such as polylacetate, polyglycolate, polycaprolactones and random co-polymers of the formulae:

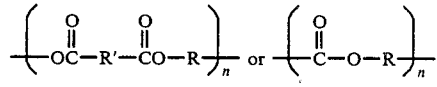

wherein n is a repeating mer unit and R and R' are alkyl, aryl, alkylene, or arylene.

The types of acids which can be used in the invention are discussed below.

Aliphatic Acids

Aliphatic acids may be represented by the general formula R—COOH wherein R is a linear or branched hydrocarbon chain containing up to 30 carbon atoms, which may consist of aliphatic and aromatic branches. Also, R can be substituted at positions 2 and/or 3 by functional groups which are electron withdrawing and serve to lower the pKa of the carboxylic group into the range of 1 to 4. Specific examples of functional groups are:

—OH, —OMe, OEt, —OR', —COOH, —COOMe, —COOEt, —COOR', —CONH₂, —CONHR₁, —CONR₂', —Cl, —F, —NO₂, —H, —CF₃,

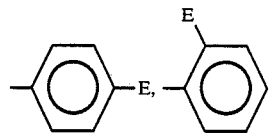

where R' denotes an alkyl group containing up to thirty (30) carbon atoms and E denotes an electron withdrawing group. Specific examples of aliphatic acids are:
2-fluorostearic acid,
2-fluoropalmitic acid,
2-fluoromyristic acid,
2-nitrostearic acid,
2,2-difluorostearic acid and
2,3-difluorostearic acid.

Aromatic Carboxylic Acids

Aromatic carboxylic acids may be represented by the general formula aryl-$(COOH)_n$ where n is 1 to 4, preferably 1 or 2 and "aryl" is a benzene ring or a naphthalene structure. Aryl can bear any of the functional groups listed for aliphatic carboxylic acids at any position, preferably at positions ortho or para to the carboxylic acid functional group. These substituents are electron withdrawing and serve to bring the pKa of the carboxylic acid group into the range of 1 to 4.

Specific examples of aromatic acids are:
o-fluorobenzoic acid
p-fluorobenzoic acid
o-nitrobenzoic acid
p-nitrobenzoic acid
p-trifluoromethyl benzoic acid
o-trifluoromethyl benzoic acid
4-trifluoromethyl-1-naphthoic acid Phthalic acid monoamides which are correctly named as N,N-dialkylphthalamic acids or N-alkyl phthalamic acids may also be used. Specific examples are:
N-dodecyl phthalamic acid,
N-methyl-N-dodecyl phthalamic acid,
N-methyl-N-octadecyl phthalamic acid, and
N-octadecyl phthalamic acid, These phthalamic acids have the formula:

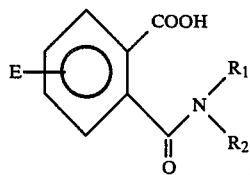

Where $R_1$ and/or $R_2 = C_{1-30}$ or H but both $R_1$ and $R_2$ cannot be hydrogen. E denotes an electron withdrawing group or hydrogen.

Also included are polymers from which carboxylic acid groups are pendent.

Suitable drugs (therapeutics) and beneficial substances (biologically active agents) for incorporation into or to be surrounded by the polymer matrix to be used with this invention and to be released to an aqueous environment include without limitation, the following: pesticides, herbicides, germicides, biocides, algicides, rodenticides, fungicides, insecticides, antioxidants, plant growth promoters, fertilizers, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, vaccines and other agents that benefit that environment of use.

In the specification and the accompanying claims, the term "drug" includes any physiologically or pharmacologically active substances that produce a localized or systemic effect or effects in animals, which term includes mammals, humans and primates. The term also includes domestic household, sport or farm animals such as sheep, goats, cattle, horses, chickens, turkeys and pigs, for administering to laboratory animals such as mice, rats and guinea pigs, and to fishes, to avians, to reptiles and zoo animals. The term "physilogically" as used herein denotes the administration of drug to produce normal levels and functions. The term "pharmacologically" denotes variations in response to amounts of drug including therapeutics. *Stedman's Medical Dictionary*, 1966, published by Williams & Wilkins, Baltimore, Md. The phrase drug formulation as used herein means the drug may be by itself, or the drug may be mixed with solutes, binders, dyes, mixtures thereof, and the like. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synoptic sites, neuro-effector junctional sites, endocrine and hormone systems, immunological system, reproductive system, skeletal system, autocoid systems, alimentary and excretory systems, inhibitory of autocoids and histamine systems, those materials that act on the central nervous system such as hypnotics and sedatives, including pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and α-bromoisovaleryl urea; hypnotic and sedative urethanes and disulfanes; psychic energizers such as isocoboxazid, nialamide, phenelzine, imipramine, amitryptyline hydrochloride, tranylcypromine and pargylene; and protryptyline hydrochloride, tranquilizers such as chloropromazine, promazine, fluphenzaine, reserpine, deserpidine, meprobamate, and benzodiazepines such as diazepam and chlordiazepoxide; anticonvulsants such as primidone, enitabas, phenytoin, ethyltion, pheneturide and ethosuximide; muscle relaxants and antiparkinson agents such as mephenesin, methocarbomal, cyclobenzaprine trihexylphenidyl, levodopa/carbidopa, and biperiden; antihypertensives such as α-methyldopa and L-β-3-4-dihydroxyphenylalanine, and pivaloyloxyethyl ester of α-methyldopa hydrochloride dihydrate; analgesics such as morphine, coedine, meperidine, nalorphine; antipyretics and anti-inflammatory agents such as aspirin, indomethacin, sodium indomethacin trihydrate, salicylamide, naproxen, colchicine, fenoprofen, sulindac, diflunisal, diclofenac, indoprofen and sodium salicylamide; local anesthetics such as procaine, lidocaine, maepaine, piperocaine, tetracaine and dibucane; antispasmodics and muscle contractants such as atropine, scopolamine, methscopolamine, oxyphenonium, papaverine; prostaglandins such as PGE$_1$, PGE$_2$, PGF$_{1\alpha}$, PGF$_{2\alpha}$ and PGA; antimicrobials and antiparasitic agents such as penicillin, tetracycline, oxytetracycline, chlorotetracycline, chloramphenicol, thiabendazole, ivermectin, and sulfonamides; antimalarials such as 4-aminoquinolines, 8-aminoquinolines and pyrimethamine; hormonal agents such as dexamethasone prednisolone, cortisone, cortisol and triamcinolone; androgenic steroids such as methyltestosterone, and fluoxmesterone; estrogenic steroids such as 17β-estradiol, α-estradiol, estriol, α-estradiol 3-benzoate, and 17-ethynyl estradiol-3-methyl ether; progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-(5(10)-estren-3-one, and 9β,10α-pregna-4,6-diene-3,20-dione; sympathomimetic drugs such as epinephrine, phenylpropanolamine hydrochloride, amphetamine, ephedrine and norepinephrine; hypotensive drugs such as hydralazine; cardiovascular drugs such as procainamide, procainamide hydrochloride, amyl nitrite, nitroglycerin, dipyridamole, sodium nitrate and mannitol nitrate; diuretics such as chlorothiazide, acetazolamide, methazolamide, hydrochlorothiazide, amiloride hydrochloride and flumethiazide, ethacrynic acid, furosemide; antiparasitics such as bephenium, hydroxynaphthoate, dichlorophen and dapsone; and neoplastics such as mechlorethamine, uracil mustard, 5-fluorouracil, 6-thioguanine and procarbazine; β-blockers such as pindolol, propranolol, practolol, metoprolol, oxprenolol, timolol, timolol maleate, atenolol, alprenolol, and acebutolol; hypoglycemic drugs such as insulin, isophane insulin, protamine zinc insulin suspension, globin zinc insulin, extended insulin zinc suspension, tolbutamide, acetohexamide, tolazamide and chlorpropamide; antiulcer drugs such as cimetidine; nutritional agents such as ascorbic acid, niacin, nicotinamide, folic acid, choline, biotin, pantothenic acid, and vitamin B$_{12}$; essential amino acids; essential fats; eye drugs such as timolol, timolol maleate, pilocarpine, pilocarpine salts such as pilocarpine nitrate, pilocarpine hydrochloride, dichlorophenamide, atropine, atropine sulfate, scopolamine and eserine salicylate; histamine receptor antagonists such as cimetidine; and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumarate and sodium lactate; and drugs that act on α-adrenergic receptors such as clonidine hydrochloride.

Additional preferred drugs include quinoline and naphthyridine carboxylic acids and related compounds, such as 1-ethyl-6-fluoro-1,4-dihydro-4-oxo-7-(1-piperazinyl)-3-quinolinecarboxylic acid; 1-ethyl-1,4-dihydro-7-methyl-4-oxo-1,8-naphthyridine-3-carboxylic acid; 5-ethyl-5,8-dihydro-8-oxo-1,3-dioxolo-[4,5-g]quinoline-7-carboxylic acid; 8-ethyl-5,8-dihydro-5-oxo-2-(1-piperazinyl)pyrido[2,3-d]pyrimidine-6-carboxylic acid; 9-fluoro-6,7-dihydro-5-methyl-1-oxo-1H,5H-benzo[ij]quinoxolizine-2-carboxylic acid; 1-ethyl-1,4-dihydro-4-oxo-7-(4-pyridinyl)-3-quinolinecarboxylic acid; 1-ethyl-1,4-dihydro-4-oxo-[1,3]dioxolo[4,5-g]cinnoline-3-carboxylic acid; 9-fluoro-3-methyl-10-(4-methyl-1-piperazinyl)-7-oxo-2,3-dihydro-7H-pyrido[1,2,3-de][1,4]benzoxazine-6-carboxylic acid; 1-ethyl-6-fluoro-1,4-dihydro-7-(4-methyl-1-piperazinyl)-4-oxo-1,8-naphthyridine-3-carboxylic acid; 1-ethyl-6-fluoro-1,4-dihydro-7-(1-piperazinyl)-4-oxo-1,8-naphthyridine-3-carboxylic acid; 1-cyclopropane-6-fluoro-1,4-dihydro-4-oxo-7-(1-piperazinyl)-3-quinolinecarboxylic acid; 1-methylamino-6-fluoro-1,4-dihydro-4-oxo-7-(4-methyl-1-piperazinyl)-3-quinolinecarboxylic acid; 1-(4-fluoro-1-phenyl)-6-fluoro-1,4-dihydro-4-oxo-7-(1-piperazinyl)-3-quinolinecarboxylic acid; 1-(4-fluoro-1-phenyl)-6-fluoro-1,4-dihydro-4-oxo-7-(4-methyl-1-piperazinyl)-3-quinolinecarboxylic acid; 1-(4-fluoro-1-phenyl)-6-fluoro-1,4-dihydro-4-oxo-7-(1-piperazinyl)-1,8-naphthyridine-3-carboxylic acid; and 1-ethyl-6-fluoro-1,4-Dihydro-4-oxo-7-(3-ethylaminomethyl-1-pyrrolidinyl)-8-fluoro-3-quinolinecarboxylic acid.

Additional preferred drugs include drugs which affect the respiratory tract such as budesonide, enprofylline, tranilast, albuterol, theophylline, aminophylline, brompheniramine, chlorpheniramine, promethazine, diphenhydramine, azatadine, cyproheptadine, terbutaline, metaproterenol, and isoproterenol; drugs which are antidepressants such as amiflamine, alaproclate, doxepin, trazedone, maprotiline, zimelidine, fluvoxamine; antipsychotic drugs such as haloperidol, thioridazine, trifluoperazine, MK-0212, and remoxipride; sedative hypnotic and antianxiety drugs such as triazolam, temazepam, chlorazepate, alproazolam, diazepam, flurazepam, lorazepam, oxazepam, hydroxyzine, prazepam, meprobamate, butalbital, and chlorzoxazone; antiparkinson drugs such as benztropine and L-647,339; hormonal and steroidal drugs such as conjugated estrogens, diethylstilbesterol, hydroxyl progesterone, medroxy progestrone, norethindrone, betamethasone, methylprednisolone, prednisone, thyroid hormone, levothyroxine and MK-0621; antihypertensive and cardiovascular drugs such as isosorbide dinitrate, digoxin, nadolol, disopyramide, nifedipine, quinidine, lidocaine, diltiazam, verapamil, prazosin, captopril, enalapril, lisinopril, metyrosine, felodipine, tocainide, mexiletine, mecamylamine, and metyrosine; diuretic drugs such as spironolactone, chlorthalidone, metolazone, triamterene, methylclothiazide, and indacrinone, antiinflammatory drugs such as ibuprofen, phenylbutazone, tolmetin, piroxicam, melclofenamate, auranofin, flurbiprofen and penicillamine; analgesic drugs such as acetaminophen, oxycodone, hydrocodone, and propoxyphene; antiinfective drugs such as cefoxitin, cefazolin, cefotaxime, cephalexin, nicarbazin, amprolium, ampicillin, amoxicillin, cefaclor, erythromycin, nitrofurantoin, minocyline, doxycycline, cefadroxil, miconazole clotrimazole, phenazopyridine, clorsulon, fludalanine, pentizidone, cilastin, phosphonomycin, imipenem, arprinocid, and foscarnet; gastrointestinal drugs such as bethanechol, clidinium, dicyclomine, meclizine, prochlorperizine, trimethobenzamide, loperamide, ranitidine, diphenoxylate, famotidine, metoclopramide and omeprazole; anticoagulant drug such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, trimethoprim, lovastatin, mevinolin, and ivermectin.

The above list of drugs is not meant to be exhaustive. Many other drugs will certainly work in the instant invention.

Examples of beneficial drugs are disclosed in *Remington's Pharmaceutical Sciences,* 16th Ed., 1980, published by Mack Publishing Co., Easton, Penna.; and in *The*

*Pharmacological Basis of Therapeutics,* by Goodman and Gilman, 6th Ed., 1980, published by The MacMillian Company, London.

The drug can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the form of a solution, dispersion, paste, cream, particle, granule, emulsion, suspension or powder. Also, the agent can be mixed with a binder, dispersant, emulsifier or wetting agent and dyes.

The amount of drug or beneficial substance incorporated into the polymer matrix will vary greatly depending on the particular drug, the desired therapeutic effect and the time span in which the polymer matrix is eroded to release the particular drug. Thus, there is no critical upper limit on the amount of drug incorporated in the polymer matrix and the lower limit will also depend on the activity of the drug and the time span for the erosion of the polymer and subsequently the drug release. Thus, it is not practical to define a range for the therapeutically effective amount of drug to be incorporated in the novel polymer matrices and acid combinations of the instant invention. However, in general the drug may be 0.001% up to 70%, by weight, of the polymer/acid matrix by weight.

When the erodible polymer/acid matrix surrounds a drug formulation core as a coating or film to create a device the device can house from 0.05 mg to 5 grams or more the drug formulation. The weight of the erodible polymer/acid matrix serving as the coating will vary depending on the surface area to be covered and the thickness needed to achieve the desired drug release profile. Typically the coat will be 10 to 1,000 microns thick although thicker and thinner fall within the invention.

The amount of acid incoporated into the polymer will be dependent upon the release duration of the drug or beneficial substance, and the particular acid used but would generally be in the range of slightly more than 0%, preferably 0.001% to a maximum of about 25%, by weight, of the polymer by weight.

The drug or beneficial substance can be administered in various ways and shapes. For example, the polymer/acid/drug or beneficial substance can be incorporated into disc-shaped devices, rods or sheets for under the skin implantation, spherical shapes and the like. Those skilled in the art would realize that the invention can be incorporated in any shaped device for the particular application it is being used for.

The above described devices can be prepared by, for example:

1. Methods of preparation include:
   (1) Dissolution of components in solvent, evaporation of solvent, compression of matrix; (2) Mechanical milling of polymer, acid and drug or beneficial substance followed by compression; (3) Melt mixing of polymer, acid or drug or beneficial substance. In all cases, after mixing, standard pharmaceutical and plastics processing technology is used to make the dosage form.

In order to control the rate of release of the drug or beneficial substance in a programmable manner, one can laminate layers wherein the polymer, acid and drug or beneficial substance in each laminate layer are varied in concentration or contain different species of each component.

Multiple acids can be incorporated into the polymer to allow time variable or geometric considerations to be achieved. Additionally, the concentration of acid can be varied as a function of position in the matrix.

At least enough water must contact the device to react with the acid and the polymer to cause erosion. Water in excess of this amount will not materially effect the performance of the invention.

Several studies which demonstrate advantages of employing a free acid rather than an acid anhydride in promoting erosion of poly(ortho ester) drug delivery matrices are shown below.

TABLE 1

Catalyst destruction upon incorporation into a poly(ortho ester) drug delivery matrix.

| Erosion Catalyst | % w/w catalyst added | % w/w catalyst remaining after Processing | % catalyst destroyed |
|---|---|---|---|
| free acid: | | | |
| 2-fluorostearic acid + poly(ortho ester) | 4.60 | 4.59 | 0.22 |
| anhydride: | | | |
| phthalic anhydride + poly(ortho ester) + | 3.00 | 2.80 | 6.67 |
| + cyclobenzaprine HCl (drug) | 3.00 | 1.01 | 66.33 |

| | |
|---|---|
| Summary: | The loss of catalyst after processing is 30 times higher with anhydride versus free acid when no drug is present. Adding drug results in a 66.33% loss of anhydride. |
| Conclusion: | Anhydrides react significantly with both the polymer and added drugs, consuming the catalyst and creating new unwanted chemical derivatives of unknown toxicity in an uncontrollable manner. This problem is eliminated through direct use of free acids as the catalyzing species. |

Reaction of Phthalic Anhydride with Poly(ortho ester) matrices containing 0–7.5% w/w cyclobenzaprine HCl (drug).

Figure 2:
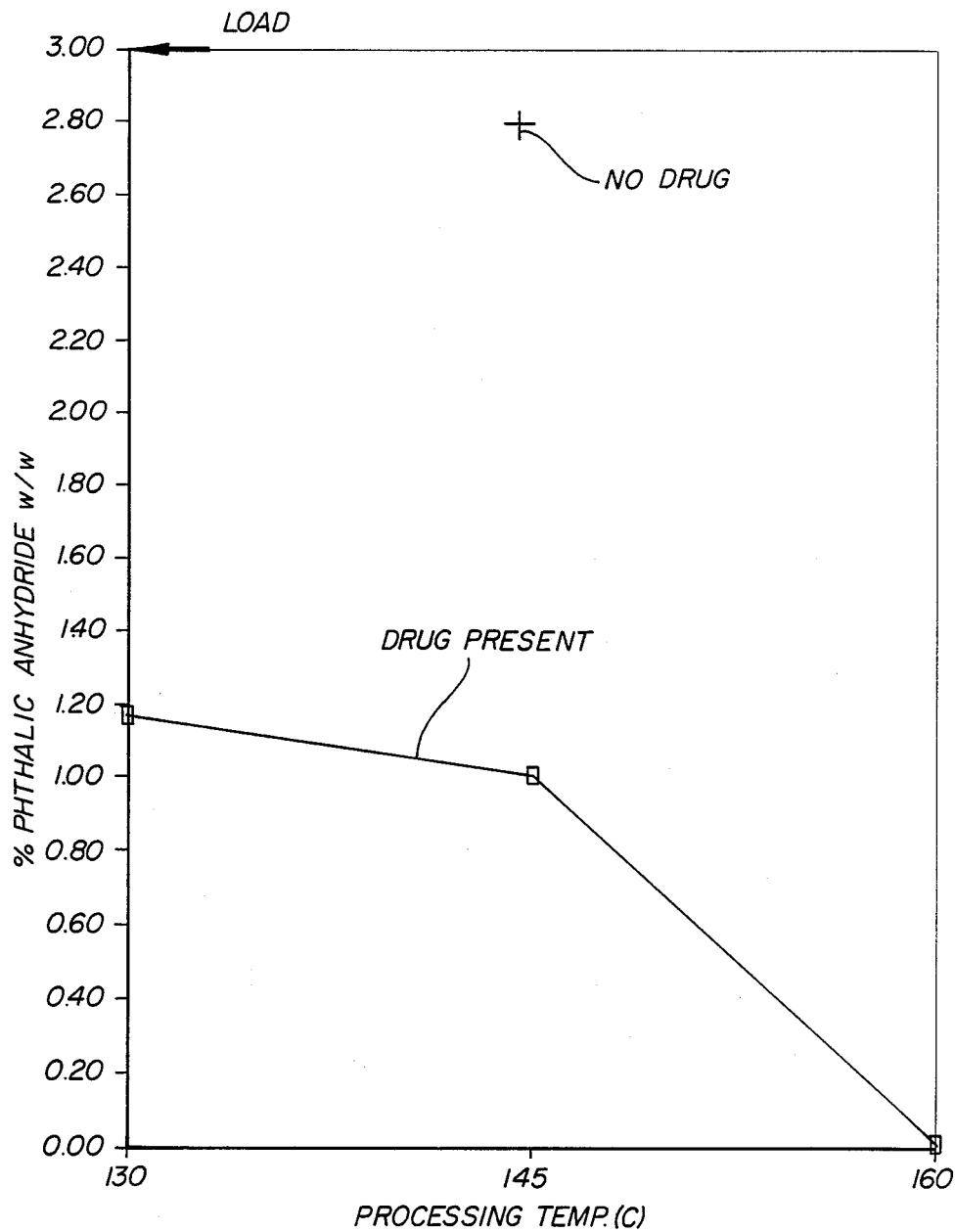
Figure 3:
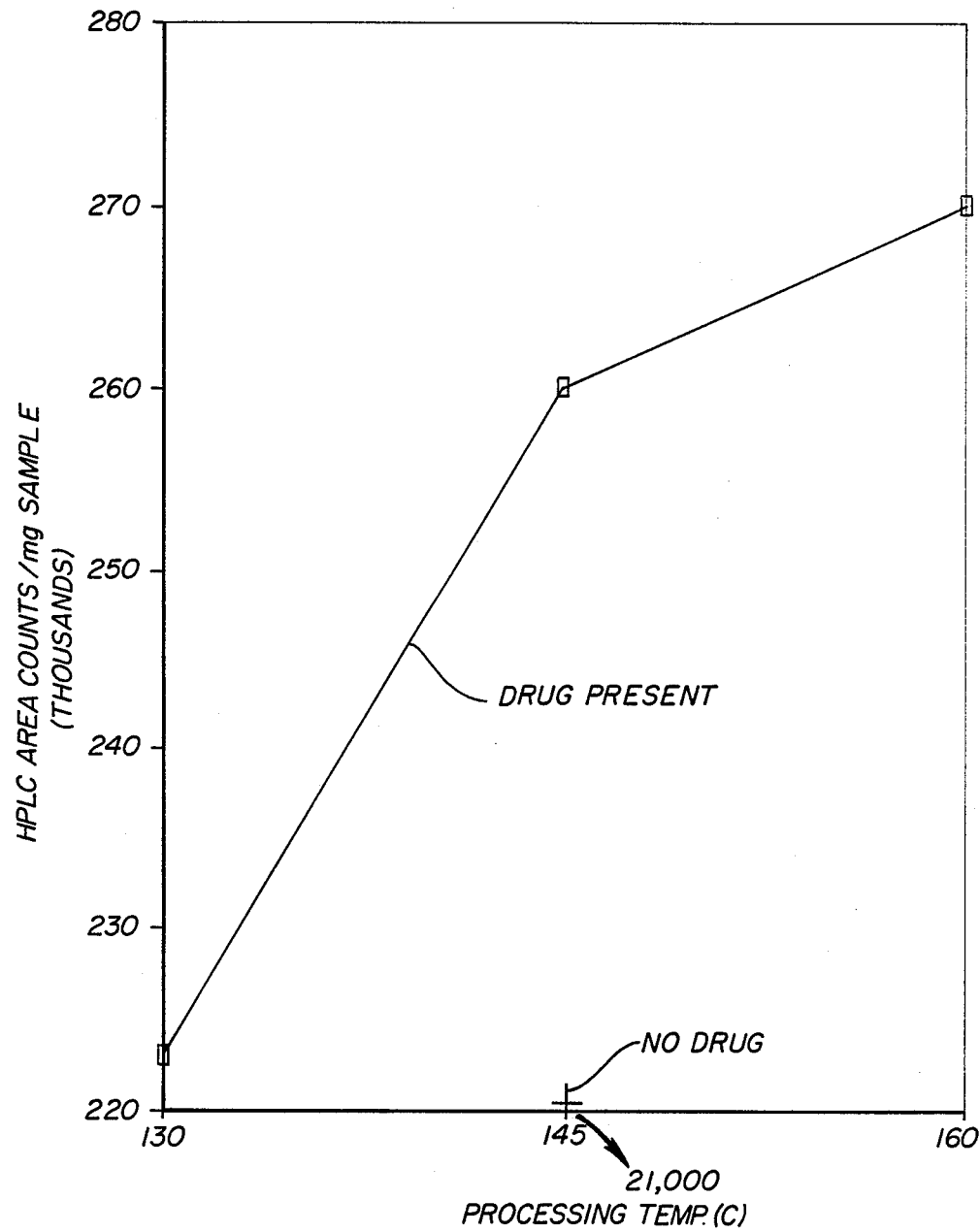
Figure 4:
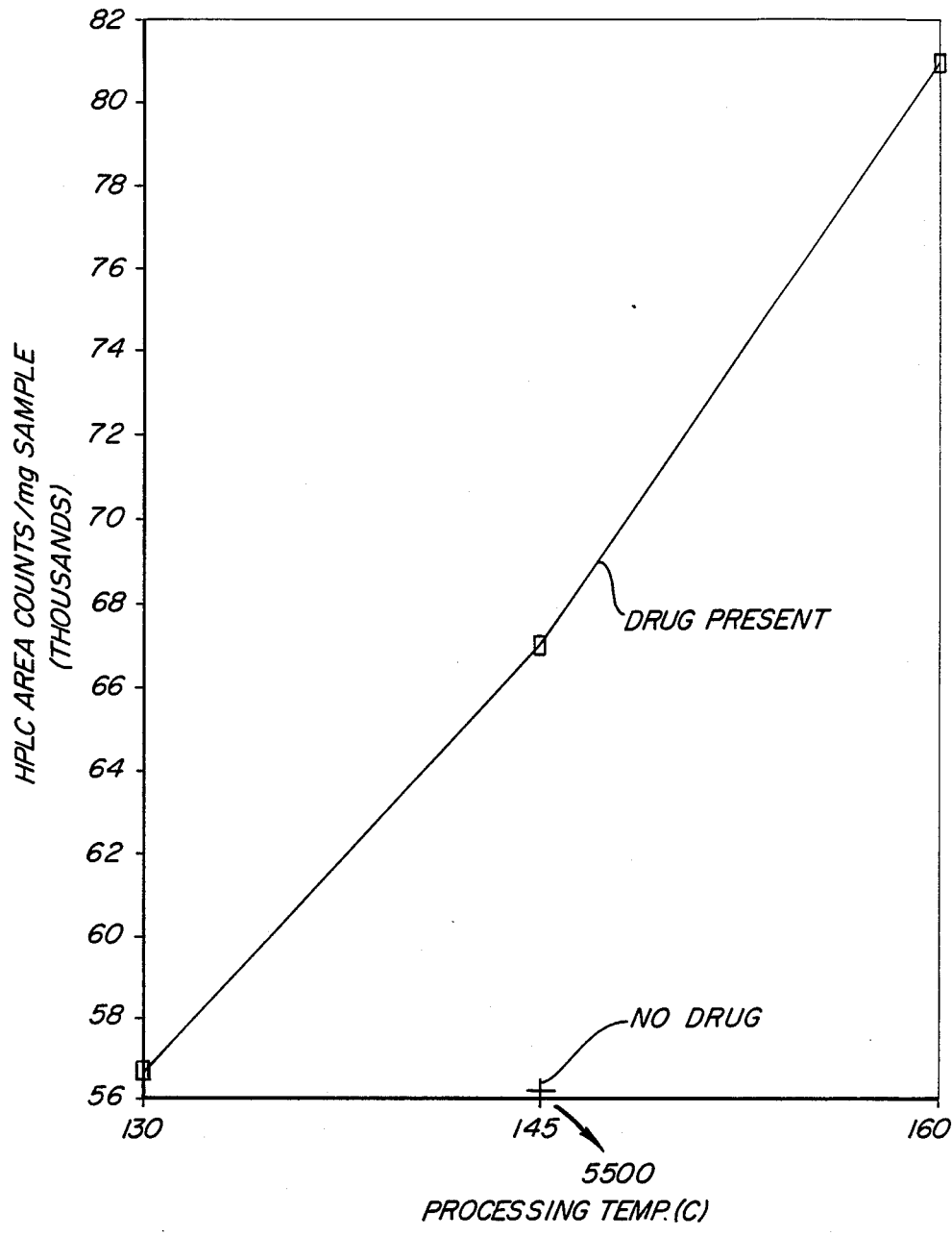

FIG. 1 compares the infrared spectra of thin films of poly(ortho ester) (POE) polymer into which 3% w/w phthalic anhydride (PA) and 0–7.5% w/w cyclobenzaprine HCl (FLX) have been added. The composite POE/PA/FLX materials were thermally mixed then solvent cast from methylene chloride onto sodium chloride plates for use in the infrared (IR) instrument. In trace spectrum I. the peaks at 1853, 1789, and S1777 are due to phthalic anhydride. The absorbance at 1735 is characteristic of phthalate esters such as hexanediol monophthalate and cyclohexanedimethanol monophthalate which can result from reaction of PA with the POE polymer. Trace spectra II., III., and IV. show a progressive disappearance of the characteristic phthalic anhydride peaks with a pronounced increase in the intensity of the phthalate derivative(s) peak at 1735 with incorporation of the drug FLX; increases in the processing temperature accentuate the effect. This agrees with the data of Table 1 and the data presented in FIGS. 2-4 which clearly indicate that phthalic anhydride is consumed during standard polymer processing procedures to form the phthalate derivatives hexanediol monophthalate and cyclohexanedimethanol monophthalate. Thus, PA, and anhydrides as a class, are unacceptable catalysts for the POE matrix due to extreme reactivity leading to catalyst loss and unreliable performance of the composite as a drug releasing system. Additionally, an incorporated anhydride does not lead to a corresponding amount of acid catalyst upon exposure to water due to the formation of chemical derivatives during processing and storage.

Unexpected Advantages of Free Acids as a Catalyst

1. Free acid catalysts can be directly incorporated into the poly(ortho ester) matrix with minimal loss of catalyst (0.22%) and minimal loss of polymer molecular weight (before catalyst introduced molecular wt. is 32,000±4,000; after incorporation of 2-fluorostearic acid the molecular wt. was 29,000±2,000). Anhydride catalysts show a large loss of catalyst (>66%) upon introduction into the poly(ortho ester) matrix that can be attributed to the extreme reactivity of the anhydrides as acylating agents. Significant molecular weight losses of the polymer are routinely observed when using anhydride catalysts.

2. Free acids having the appropriate pKa, m.p., and hydrophobicity as defined herein have been shown to lower the glass transition temperature of the poly(ortho ester) polymer by approximately 30° C., permitting processing procedures which subject the polymer/drug/catalyst composite to markedly less heat and shear stress than encountered when anhydrides are used as catalysts. Free acids act to plasticize the polymer matrix in addition to having minimal chemical reactivity with the drug or polymer.

In order to better describe this invention, there follows examples illustrating the concepts of the invention.

EXAMPLE 1

Figure 5:
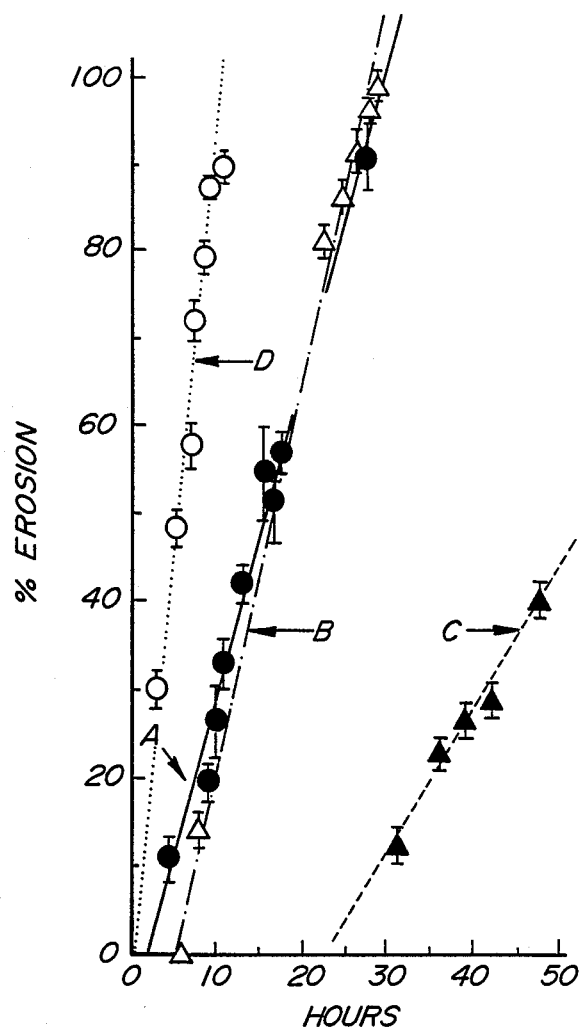

960.0 mg of the acid labile polymer DETOSU-1,6-hexanediol:trans-cyclohexanedimethanol (65:35) were combined with 40.0 mg (0.12 mmoles) of the acid catalyst N-dodecyl phthalamic acid (m.p. 84°-86° C.) to make a final acid catalyst concentration of 4% N-dodecyl phthalamic acid, based on the polymer weight, then mixed for three minutes or until a homogeneous dispersion was achieved using a commercial mechanical shaker (WIG-L-BUG, Crescent Dental Manuf. Co.). The powdered mixture was placed in a Custom Scientific Mini Max Injection Molder pre-heated to 120°-130° C., mixed for 1.5 minutes until the mixture was molten, then injected into a heated die (130° C.) containing three cavities each 1 cm in diameter and three mm thick. The die was rapidly cooled to room temperature with dry ice. The discs were removed from the die. Each disc was placed in 200 ml of 0.05M phosphate buffer, 37° C., pH 7.4, in standard USP dissolution vessels and agitated at 100 rpm using a DS500S stirrer (MEDIX Technologies, Inc.). Erosion of the discs was followed by assaying for one of the polymer's degradation products, 1,6-hexanediol, using an HP5880A gas chromatograph. The discs eroded at a zero-order rate of 3.52% per hour with a lag time of 1.9 hours (see FIG. 5, curve A). Polymer containing no added acidic catalyst did not measurably erode over the same time course.

EXAMPLE 2

948.2 mg of the acid labile polymer DETOSU-1,6-hexanediol:trans-cyclohexanedimethanol (65:35) were combined with 51.8 mg (0.12 mmoles) of the acid catalyst N-methyl-N-octadecyl phthalamic acid (m.p. 70°-72° C.) to make a final acid catalyst concentration of 5.2% N-methyl-N-octadecyl phthalamic acid, based on polymer weight. The combination was mixed and injection molded as in Example 1; the same dissolution procedure and gas chromatographic assay was used to analyze the discs' erosion. The discs eroded at a zero-order rate of 4.2% per hour with a lag time of 5.1 hours (see FIG. 5, curve B). Polymer containing no added acidic catalyst did not measurably erode over the same time period.

EXAMPLE 3

973.0 mg of the acid labile polymer DETOSU-1,6-hexanediol; trans-cyclohexanedimethanol (65:35) were combined with 27.0 mg (0.12 mmole) of the acid catalyst N-butyl phthalamic acid (m.p. 97°-98° C.) to make a final acid catalyst concentration of 2.7% N-butyl phthalamic acid, based on polymer weight. The combination was mixed and injection molded as in Example 1; the same dissolution procedure and gas chromatographic assay was used to analyze the discs' erosion. The discs eroded at a zero-order rate of 1.6% per hour with a lag time of 22.8 hours (see FIG. 5, curve C). Polymer containing no added acidic catalyst did not measurably erode over the same time course.

EXAMPLE 4

980.0 mg of the acid labile polymer DETOSU-1,6-hexanediol:trans-cyclohexanedimethanol (65:35) were combined with 20.0 mg (0.12 mmoles) of the acid catalyst phthalic acid (m.p. 230° C.) to make a final acid catalyst concentration of 2% phthalic acid, based on polymer weight. The combination was mixed and injection molded as in Example 1; the same dissolution procedure and gas chromatographic assay was used to analyze the discs' erosion. After 4 days, the discs were approximately 90% eroded. Polymer containing no added acidic catalyst did not measurably erode over the same time course.

EXAMPLE 5

Rates of drug release from acid catalysed poly(ortho ester) matrices and rates of erosion of the polymer were correlated. The matrices were DETOSU-1,6-hexanediol:trans-cyclohexanedimethanol (65:35) polymer discs containing 3.5% w/w hydrochlorothiazide (HCTZ) as a model drug and 4% w/w 2-fluorostearic acid (FSA) as the catalyst for erosion. The discs were 1 cm in diameter, 0.3 cm thick, and weighed an average of 300 mg. after injection molding. The in vitro release of HCTZ from three disks was monitored in a U.S.P. Dissolution Method No. 2 apparatus (pH 7.4; 37° C.) using an HPLC analytical technique. The release profiles were reproducible between batches and were linear (zero-order kinetics) for approximately 14 hours (greater than 90% of initial drug load released) with a HCTZ release rate of approximately 7% per hour. This correlated well with stuides of polymer erosion using FSA as catalyst; polymer erosion occurred at a rate of 7-8% per hour.

EXAMPLE 6

942.2 mg of the acid labile polymer DETOSU-1,6-hexanediol:trans-cyclohexanedimethanol (65:35) were combined with 57.8 mg (0.12 mmole) of the acid catalyst N-methyl-N-octadecyl-5-nitro-phthalamic acid (m.p. 68°–70° C.) to make a final acid catalyst concentration of 5.8% N-methyl-N-octadecyl-5-nitrophthalamic acid, based on polymer weight. The combination was mixed and injection molded as in Example 1; the same dissolution procedure and gas chromatographic assay was used to analyze the discs' erosion. The discs eroded at a zero order rate of 9.9% per hour with a lag time of 0.61 hours (see FIG. 5, curve D). Polymer containing no added acidic catalyst did not measurably erode over the same time course.

What is claimed is:

1. A controlled release device for the delivery of drugs or other biological beneficial substances which comprises:
   (a) an acid labile polymer, and
   (b) an erosion catalyzing amount up to a maximum of about 25 percent, by weight, based on (a), of at least one organic carboxylic acid and mixtures thereof selected from the group consisting of 2-fluorostearic acid, 2-fluoropalmitic acid, 2-fluoromyristic acid, 2-nitro-stearic acid, 2,2-difluorostearic acid, 2,3-difluorostearic acid, o-fluorobenzoic acid, p-fluorobenzoic acid, o-nitrobenzoic acid, p-nitrobenzoic acid, p-trifluoromethyl benzoic acid, o-trifluoromethyl benzoic acid, 4-trifluoromethyl-1-naphthoic acid, N-dodecyl phthalamic acid, N-methyl-N-dodecyl phthalamic acid, N-methyl-N-octadecyl phthalamic acid, N-octadecyl phthalamic acid, N-butyl-phthalamic acid, and N-methyl-N-octadecyl-5-nitro-phthalamic acid incorporated within the matrix of said acid labile polymer.

2. The controlled drug release device of claim 1, further comprising an effective amount up to 70 percent, by weight, based on (a) and (b), of a drug or other biologically beneficial substance incorporated within or surrounded by the matrix of said acid labile polymer.

3. The controlled drug release device of claim 2, wherein the drug or biological beneficial substance is a protein drug, a desensitizing agent, a vaccine, an anti-infective, an antiallergenic, a steroidal anti-inflammatory, a decongestant, a miotic, an anticholinergic, a sympathomimetic, a sedative; a hypnotic, a psychic energizer, a tranquilizer, an androgenic steroid, an estrogen, a progestational agent, a humoral agent, an antipyretic analgesic, an antispasmotic, an antimalarial, an antihistamine, a cardioactive agent, a non-steroidal anti-inflammatory, an antiparkinsonian agent, an antihypertensive agent, a β-adrenergic blocking agent, a nutritional agent, a herbicide, a pesticide, a biocide, a fertilizer or an antifouling compound.

4. The controlled drug release device of claim 1, wherein said acid labile polymer is a polymer of di(or a higher functionality) ketene acetal and polyols of the formula:

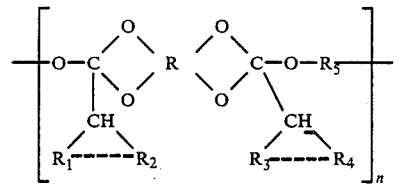

wherein n is an integer substantially greater than 10; and wherein $R_1$ and $R_2$ are hydrogen or the same or different essentially hydrocarbon groups and may be separate groups or may form parts of a cyclic group; R is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other similar chains, and wherein R may be a single quadrivalent radical attached to all the interim acetal forming oxygen atoms, may be a spiro structure, may be an open chain aliphatic group, or may contain a carbocyclic group and wherein additionally, $R_5$ may contain some mer units that are alkylene or contain a carbocyclic group and including polymers having the repeat units

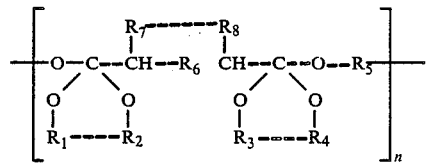

wherein n is an integer substantially greater than 10; wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group; $R_5$ is an essentially hydrocarbon group which is the residue of a polyol $R_5(OH)_a$ wherein a is an integer equal to two or more, such polyol being a single molecular species or a mixture of molecular species; $R_6$ is a valence bond or an essentially hydrocarbon group; $R_7$ and $R_8$ are hydrogen or essentially hydrocarbon groups which may be separate groups or may form parts of a cyclic group; and wherein such linear chains may be crosslinked to similar chains and wherein the group

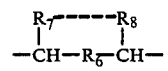

may be selected from the classic alkylene end groups containing a carbocyclic ring.

5. The controlled drug release device of claim 1, wherein said acid labile polymer is a polyorthocarbonate of the formula

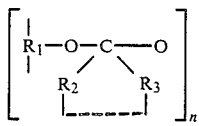

wherein $R_1$ is a multivalent hydrocarbon radical, $R_2$ and $R_3$ are hydrocarbon radicals with at least one of $R_2$ and $R_3$ bonded to the dioxycarbon through an oxygen linkage and n is a repeating mer unit.

6. The controlled drug release device of claim 1, wherein said organic acid is selected from the group consisting of 2-fluorostearic acid, p-trifluoromethyl benzoic acid, N-dodecyl phthalamic acid, N-octadecyl phthalamic acid, N-methyl-N-octadecyl phthalamic acid, N-butyl phthalamic acid, and the corresponding terephthalamic acid derivatives, phthalic acid, and N-methyl-N-octadecyl-5-nitro-phthalamic acid.

7. The controlled drug release device of claim 1, wherein said acid labile polymer is a polymer of DETOSU 1,6-hexanediol/trans cyclohexanedimethanol wherein DETOSU is 3,9-bis(ethylidene)-2,4,8,10-tetraoxospiro[5,5]-undecane.

8. A process for catalyzing the erosion of an acid liable polymer, comprising incorporating within the matrix of an acid labile polymer an erosion catalyzing amount up to a maximum of about 25 percent by weight, based on the weight of said acid labile polymer, of at least one organic carboxylic acid and mixtures thereof selected from the group consisting of 2-fluorostearic acid, 2-fluoropalmitic acid, 2-fluoromyristic acid, 2-nitro-stearic acid, 2,2-difluorostearic acid, 2,3-difluorostearic acid, o-fluoro-benzoic acid, p-fluorobenzoic acid, o-nitrobenzoic acid, p-nitrobenzoic acid, p-trifluoromethyl benzoic acid, o-trifluoromethyl benzoic acid, 4-triflu-oromethyl-1-naphthoic acid, N-dodecyl phthalamic acid, N-octadecyl phthalamic acid N-methy-N-dodecyl phthalamic acid, N-methyl-N-octadecyl phthalamic acid, N-butyl phthalamic acid, and N-methyl-N-octadecyl-5-nitro-phthalic acid.

9. The process for catalyzing the erosion of an acid labile polymer of claim 8, wherein said acid labile polymer is a polymer of di(or a higher functionality) ketene acetals and polyols of the formula:

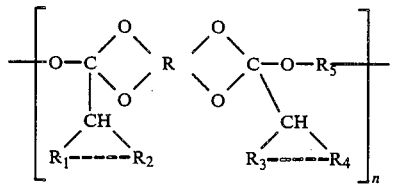

wherein n is an integer substantially greater than 10; and wherein $R_1$ and $R_2$ are hydrogen or the same or different essentially hydrocarbon groups and may be separate groups or may form parts of a cyclic group; R is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other similar chains, and wherein R may be a single quadrivalent radical attached to all the interim acetal forming oxygen atoms, may be a spiro structure, may be an open chain aliphatic group, or may contain a carbocyclic group and wherein additionally, $R_5$ may contain some mer units that are alkylene or contain a carbocyclic group and including polymers having the repeat units

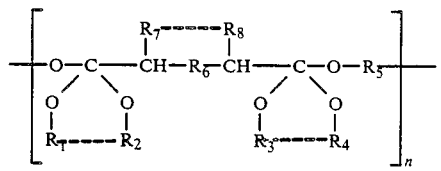

wherein n is an integer substantially greater than 10; wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group; $R_5$ is an essentially hydrocarbon group which is the residue of a polyol $R_5(OH)_a$ wherein a is an integer equal to two or more, such polyol being a single molecular species or a mixture of molecular species; $R_6$ is a valence bond or an essentially hydrocarbon group; $R_7$ and $R_8$ are hydrogen or essentially hydrocabon groups which may be separate groups or may form parts of a cyclic group; and wherein such linear chains may be crosslinked to similar chains and wherein the group

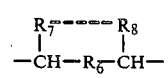

may be selected from the classic alkylene end groups containing a carbocyclic ring.

10. The process for catalyzing the erosion of an acid labile polymer of claim 8, wherein said acid labile polymer is a polyorthocarbonate of the formula:

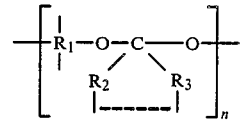

wherein $R_1$ is a multivalent hydrocarbon radical, $R_2$ and $R_3$ are hydrocarbon radicals with at least one of $R_2$ and $R_3$ bonded to the dioxycarbon through an oxygen linkage and n is a repeating mer unit.

11. The process for catalyzing the erosion of an acid labile polymer of claim 8, wherein said organic acid is selected from the group consisting of 2-fluorostearic acid, p-trifluoromethyl benzoic acid, N-dodecyl phthalamic acid, N-octadecyl phthalamic acid, N-methyl-N-octadecyl phthalamic acid, N-butyl phthalamic acid, and the corresponding terephthalamic acid derivatives, phthalic acid, dodecylbenzenesulfonic acid, and N-methyl-N-octadecyl-5-nitro-phthalamic acid.

* * * * *